US00PP17585P2

(12) United States Plant Patent
Hofmann

(10) Patent No.: US PP17,585 P2
(45) Date of Patent: Apr. 10, 2007

(54) **NEW GUINEA *IMPATIENS* PLANT NAMED 'FISCO SWERED'**

(50) Latin Name: *Impatiens hawkeri*
Varietal Denomination: Fisco Swered

(76) Inventor: Birgit Christa Hofmann, Gassenweg 29, 56170 Bendorf (DE)

( * ) Notice: Subject to any disclaimer, the term of this patent is extended or adjusted under 35 U.S.C. 154(b) by 0 days.

(21) Appl. No.: 11/241,479

(22) Filed: Sep. 30, 2005

(51) Int. Cl.
*A01H 5/00* (2006.01)

(52) U.S. Cl. ..... Plt./318
(58) Field of Classification Search ..... Plt./318
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of New Guinea *Impatiens* plant named 'Fisco Swered', characterized by its relatively compact, outwardly spreading and uniformly mounded plant habit; rounded growth habit; freely branching and freely flowering habit; medium green-colored foliage; large red and light pink bi-colored flowers; and flowers that are positioned above or beyond the foliage.

1 Drawing Sheet

Botanical designation: *Impatiens hawkeri.*
Cultivar denomination: 'Fisco Swered'.

BACKGROUND OF THE INVENTION

The present Invention relates to a new and distinct cultivar of New Guinea *Impatiens* plant, botanically known as *Impatiens hawkeri,* and hereinafter referred to by the name 'Fisco Swered'.

The new *Impatiens* is a product of a planned breeding program conducted by the Inventor in Hillscheid, Germany and Galdar, Canary Islands, Spain. The objective of the breeding program is to develop new compact *Impatiens* cultivars that flower relatively early and have attractive flower coloration.

The new *Impatiens* originated from a cross-pollination made by the Inventor during the summer of 2000 in Hillscheid, Germany of the *Impatiens hawkeri* cultivar Duepetrest, disclosed in U.S. Plant Pat. No. 11,375, as the female, or seed, parent with the *Impatiens hawkeri* cultivar Harmony Raspberry Cream, not patented, as the male, or pollen, parent. The cultivar Fisco Swered was discovered and selected by the Inventor as a flowering plant within the progeny of the stated cross-pollination in a controlled environment in Galdar, Canary Islands, Spain in April, 2001.

Asexual reproduction of the new cultivar by terminal cuttings in Galdar, Canary Islands, Spain since July, 2002, has shown that the unique features of this new *Impatiens* are stable and reproduced true to type in successive generations.

SUMMARY OF THE INVENTION

The following traits have been repeatedly observed and are determined to be the unique characteristics of 'Fisco Swered'. These characteristics in combination distinguish 'Fisco Swered' as a new and distinct *Impatiens* cultivar:

1. Relatively compact, outwardly spreading and uniformly mounded plant habit; rounded growth habit.
2. Freely branching and freely flowering habit.
3. Medium green-colored foliage.

4. Large red and light pink bi-colored flowers.
5. Flowers that are positioned above or beyond the foliage.

Plants of the new *Impatiens* can be compared to plants of the female parent, the cultivar Duepetrest. In side-by-side comparisons conducted by the Inventor in Hillscheid, Germany, plants of the new *Impatiens* differed from plants of the cultivar Duepetrest in the following characteristics:

1. Plants of the new *Impatiens* were slightly smaller than plants of the cultivar Duepetrest.
2. Plants of the new *Impatiens* had longer and lighter green-colored leaves than plants of the cultivar Duepetrest.
3. Plants of the new *Impatiens* had larger flowers than plants of the cultivar Duepetrest.
4. Plants of the new *Impatiens* and the cultivar Duepetrest differed in flower color as plants of the cultivar Duepetrest had red and lighter pink bi-colored flowers.

Plants of the new *Impatiens* can be compared to plants of the male parent, the cultivar Harmony Raspberry Cream. In side-by-side comparisons conducted by the Inventor in Hillscheid, Germany, plants of the new *Impatiens* differed from plants of the cultivar Harmony Raspberry Cream in the following characteristics:

1. Plants of the new *Impatiens* were smaller than plants of the cultivar Harmony Raspberry Cream.
2. Plants of the new *Impatiens* had narrower and lighter green-colored leaves than plants of the cultivar Harmony Raspberry Cream.
3. Plants of the new *Impatiens* and the cultivar Harmony Raspberry Cream differed in flower color as flowers of plants of the cultivar Harmony Raspberry Cream were red and white bi-colored.

Plants of the new *Impatiens* can also be compared to plants of the cultivar Neptis, disclosed in U.S. Plant Pat. No. 10,321. In side-by-side comparisons conducted by the Inventor in Hillscheid, Germany, plants of the new *Impatiens* differed from plants of the cultivar Neptis in the following characteristics:

1. Plants of the new *Impatiens* were broader than plants of the cultivar Neptis.

2. Plants of the new *Impatiens* had darker green-colored leaves than plants of the cultivar Neptis.
3. Plants of the new *Impatiens* had slightly larger flowers than plants of the cultivar Neptis.
4. Plants of the new *Impatiens* and the cultivar Neptis differed in flower color.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new *Impatiens*. The photograph comprises a side perspective view of a typical flowering plant of 'Fisco Swered' grown in a container.

DETAILED BOTANICAL DESCRIPTION

The cultivar Fisco Swered has not been observed under all possible environmental conditions. The phenotype may vary somewhat with variations in environment such as temperature and light intensity, without, however, any variance in genotype.

The aforementioned photograph, following observations and measurements describe plants grown in Hillscheid, Germany, under commercial production practice in a glass-covered greenhouse. Rooted young plants were planted in 12-cm containers and the aforementioned photograph and following observations and measurements were taken about three months later. During the production of the plants, day temperatures were about 16° C. to 20° C. and night temperatures were about 16° C. In the following description, color references are made to The Royal Horticultural Society Colour Chart, 2001 Edition, except where general terms of ordinary dictionary significance are used.

Botanical classification: *Impatiens hawkeri* cultivar Fisco Swered.

Parentage:

*Female parent.*—*Impatiens hawkeri* cultivar Duepetrest, disclosed in U.S. Plant Pat. No. 11,375.

*Male parent.*—*Impatiens hawkeri* cultivar Harmony Raspberry Cream, not patented.

Propagation:

*Type cutting.*—Terminal tip cuttings.

*Time to initiate roots.*—Summer: About 10 days at 24° C. Winter: About 12 to 15 days at 21° C.

*Time to produce a rooted cutting.*—Summer: About 15 days at 24° C. Winter: About 18 to 20 days at 21° C.

*Root description.*—Fine, fibrous; 158D in color.

*Rooting habit.*—Freely branching.

Plant description:

*General appearance.*—Relatively compact, outwardly spreading and uniformly mounded plant growth habit; low and rounded growth habit; freely branching habit; bushy appearance; freely flowering. Low to moderate vigor.

*Crop time.*—From a rooted cutting, about nine weeks are required to produce finished flowering plants in 12-cm containers.

*Plant height.*—About 10.8 cm.

*Plant diameter or spread.*—About 19.5 cm.

*Lateral branches.*—Quantity per plant: About six. Length: About 6 cm to 8 cm. Diameter: About 4 mm to 6 mm. Internode length: About 1 cm to 1.5 cm. Texture: Smooth, glabrous. Color: 183B to 183C.

*Foliage description.*—Arrangement: Primarily in whorls. Length: About 11.6 cm. Width: About 3.7 cm. Shape: Elliptic. Apex: Acuminate. Base: Acute. Margin: Serrulate with ciliation. Texture, upper and lower surfaces: Smooth, slightly rugose; glabrous. Color: Developing foliage, upper surface: 137A. Developing foliage, lower surface: 139C. Fully expanded foliage, upper surface: 137A. Fully expanded foliage, lower surface: 183D. Venation, upper surface: 47B. Venation, lower surface: 185A. Petiole: Length: About 1.2 cm. Diameter: About 3 mm. Texture, upper and lower surfaces: Smooth, glabrous. Color, upper surface: 47A. Color, lower surface: 185A.

Flower description:

*Flower type and flowering habit.*—Single, large and rounded flowers. Freely and continuously flowering; usually about six to eight flowers and flower buds per lateral branch. Flowers positioned above or beyond the foliage; flowers typically face parallel to the leaf canopy. Petals not persistent; gynoecium persistent. Flowers not fragrant.

*Flower longevity.*—Flowers last about one week on the plant.

*Flowering season.*—Year-round under greenhouse conditions. Early flowering habit; plants begin flowering about nine weeks after planting.

*Flower buds.*—Length: About 2.5 cm. Diameter: About 1.7 cm. Shape: Ovoid. Color: Between, including 58B and 46C.

*Flower length.*—About 7.1 cm.

*Flower width.*—About 7.2 cm.

*Flower depth.*—About 1.2 cm.

*Petals.*—Quantity: Five per flower, imbricate. Length: Banner petals: About 2.5 cm. Lateral and base petals: About 3.4 cm to 3.6 cm. Width: Banner petal: About 4.5 cm. Lateral petals: About 3.4 cm. Base petals: About 3.8 cm. Shape: Cordate. Apex: Moderately lobed; emarginate. Base: Attenuate. Margin: Entire; undulate. Aspect: Mostly flat. Texture, upper and lower surfaces: Smooth; satiny. Color: When opening, upper surface: Ground color, 68B; stripes and banner petal blotch, 46B. When opening, lower surface: 52A. Fully opened, upper surface: Ground color, 65A to 65B; color becoming closer to 69B with development; stripes and banner petal blotch, 46B; towards base of lateral petals, 66B. Fully opened, lower surface: 52A to 52B.

*Spur.*—Quantity: One per flower. Length: About 5 cm to 6.5 cm. Diameter: At apex: About 0.5 mm. At flower: About 3 mm. Aspect: Curved. Texture: Smooth, glabrous. Color: 58D; towards the apex, 144C.

*Peduncles.*—Length: About 4 cm. Diameter: About 2.5 mm. Texture: Smooth, glabrous. Strength: Strong, flexible. Color: 144B.

*Reproductive organs.*—Androecium: Stamen number: Five fused at anthers, hooded; filaments free. Anther length: About 6 mm. Anther shape: Obovate. Anther color: 65B. Pollen amount: Moderate. Pollen color: 8D. Gynoecium: Pistil quantity: One per flower.

Pistil length: About 5 mm to 6 mm. Stigma color: 53B. Style color: 53B. Ovary: Five-celled. Ovary color: 60A.

*Seed/fruit.*—Seed and fruit development has not been observed.

Disease/pest resistance: Plants of the new *Impatiens* have not been observed to be resistant to pathogens and pests common to *Impatiens*.

Low temperature tolerance: Plants of the new *Impatiens* have been observed to tolerate night temperatures of 5° C. with 10° C. day temperatures.

It is claimed:

1. A new and distinct cultivar of New Guinea *Impatiens* plant named 'Fisco Swered', as illustrated and described.

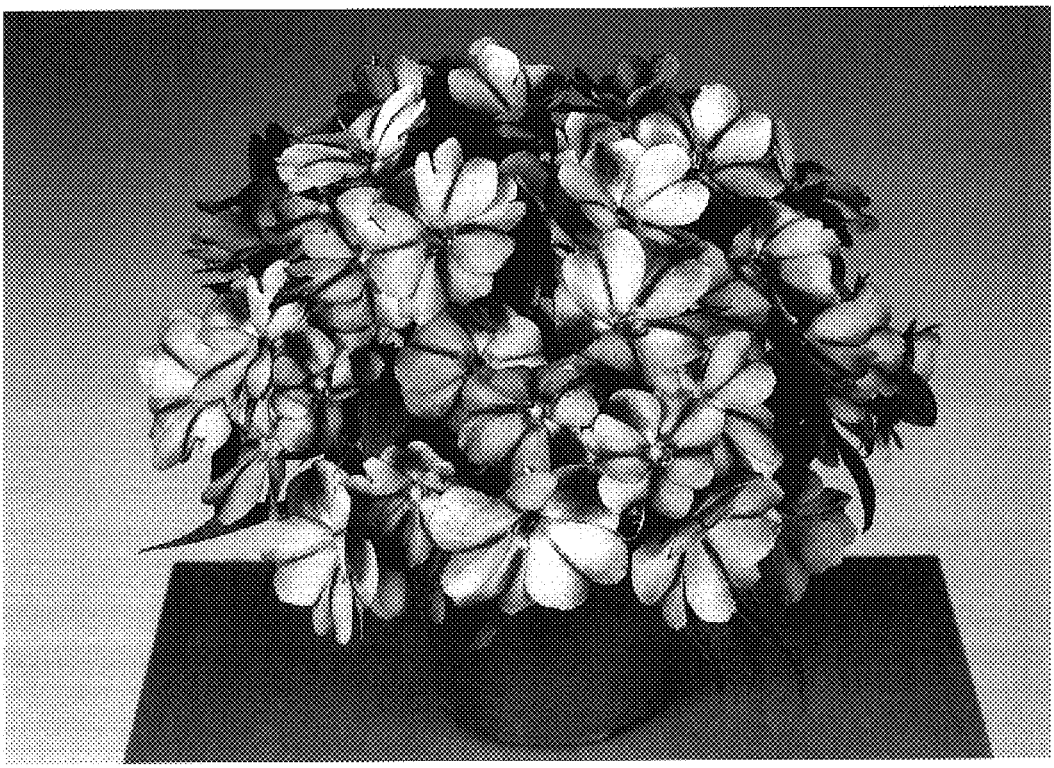

* * * * *